United States Patent
Saranathan et al.

(10) Patent No.: US 7,412,277 B1
(45) Date of Patent: Aug. 12, 2008

(54) MULTI-SLICE MR DATA ACQUISITION IN SUCCESSIVE HEARTBEATS WITH BLACK BLOOD CONTRAST

(75) Inventors: Manojkumar Saranathan, Rockville, MD (US); Glenn S. Savin, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 647 days.

(21) Appl. No.: 10/604,829

(22) Filed: Aug. 20, 2003

(51) Int. Cl.
*A61B 5/05* (2006.01)
(52) U.S. Cl. .................. 600/413; 600/410; 600/419; 600/420
(58) Field of Classification Search .............. 600/413
See application file for complete search history.

(56) References Cited

U.S. PATENT DOCUMENTS

| | | | | |
|---|---|---|---|---|
| 6,144,201 | A * | 11/2000 | Miyazaki | 324/306 |
| 6,498,946 | B1 * | 12/2002 | Foo et al. | 600/410 |
| 2003/0069493 | A1 * | 4/2003 | Pan et al. | 600/410 |
| 2004/0181146 | A1 * | 9/2004 | Yarnykh et al. | 600/419 |
| 2005/0010104 | A1 * | 1/2005 | Fayad et al. | 600/413 |

OTHER PUBLICATIONS

Song et al. Multislice Double Inversion Pulse Sequence for Efficient Black-Blood MRI. Magnetic Resonance in Medicine 47:616-620. 2002.*
Parker et al. Improved Efficency in Double-Inversion Fast Spin-Echo Imaging. Magnetic Resonance in Medicine 47:1017-1021. May 2002.*
Mani et al. A new interleaved multi-slice black blood double inversion recovery technique for vessel wall imaging. Proceedings of the Internation Society of Magnetic Resonance in Medicine. 11. Jul. 10, 2003.*

* cited by examiner

*Primary Examiner*—Brian L. Casler
*Assistant Examiner*—Parikha S Mehta
(74) *Attorney, Agent, or Firm*—Ziolkowski Patent Solutions Group, SC

(57) ABSTRACT

The invention includes a technique for efficient multi-slice image acquisition with black blood contrast in cardiac imaging such that MR data is acquired in each R-R interval of a cardiac cycle. The technique includes applying a non-selective inversion pulse, followed by a re-inversion pulse that is slice-selective over a region encompassing a plurality of slice selections. The inversion and re-inversion pulses are applied in each R-R interval. Execution of a series of RF excitation pulses in each R-R interval is timed such that signal from blood is near a null point before data acquisition.

24 Claims, 2 Drawing Sheets

MULTI-SLICE MR DATA ACQUISITION IN SUCCESSIVE HEARTBEATS WITH BLACK BLOOD CONTRAST

BACKGROUND OF INVENTION

The present invention relates generally to magnetic resonance imaging (MRI), and more particularly to, a pulse sequence, method, and apparatus for multi-slice acquisition imaging to acquire black blood contrast images during successive R-R intervals of a cardiac cycle.

MRI uses radio frequency pulses and magnetic field gradients applied to a subject in a strong homogenous magnetic field to produce viewable images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Current techniques for the acquisition of Fast Spin Echo (FSE) images with enhanced black blood contrast are limited to acquiring data in every other heartbeat. Acquiring data in this manner allows the magnetization to relax between successive inversions. For a typical cardiac examination having 256 readout points, 192 phase encodes, a three-quarter phase FOV, and an echo train length (ETL) of between 12 to 16 echoes, the scan time is typically 18 to 24 heartbeats or R-R intervals. In order to minimize respiratory artifacts, the images are acquired during an end-expiratory breath-hold. In order to achieve sufficient coverage, typically, 8 to 12 contiguous slices are acquired in successive breath-holds, which may be exhausting for the patient undergoing the MR study. Additionally, since data is acquired in alternating heartbeats, the data acquisition process is extended which negatively affects patient throughput.

It would therefore be desirable to have a technique to acquire black blood contrast images with improved acquisition for efficient imaging that is capable of imaging in successive heartbeats or R-R intervals. It would also be desirable to acquire multiple slices of MR data in each heartbeat so as to shorten data acquisition time and increase patient throughput.

BRIEF DESCRIPTION OF INVENTION

The present invention relates to an MR pulse sequence, apparatus, and a technique for efficient multi-slice acquisition with black blood contrast that solves the aforementioned problems.

The present technique includes a non-selective inversion RF pulse, followed by a broad-band slice-selective pulse that re-inverts the spins in the slab encompassing the slices to be imaged. The non-selective inversion RF pulse and the re-inversion pulse are played out in each R-R interval of a cardiac cycle during imaging. After an inversion time, RF excitation pulses are applied to acquire data for a first set of slices in the slab in an order that provides optimal blood suppression. In the next R-R interval, data for a second set of slices in the slab is acquired. The inversion time in each R-R interval is preferably selected such that the blood signal is close to the null point when data is acquired.

In accordance with one aspect of the invention, a method of multi-slice spin echo image acquisition with black blood contrast is disclosed that includes application of a non-selective inversion pulse in successive R-R intervals. The method further includes applying a re-inversion pulse in each R-R interval that is slice-selective over a region encompassing a plurality of slice selections. The method includes timing execution of a series of RF excitation pulses with spin echo readout such that signal from blood is near a null point in each R-R interval. Data is then acquired for at least one slice in each R-R interval.

In accordance with another aspect of the invention, a pulse sequence for use in multi-slice MR data acquisition includes a non-selective inversion pulse applicable to a slab of slices. The non-selective inversion pulse is designed to be applied in each R-R interval. The pulse sequence further includes a slice-selective re-inversion pulse applicable to the slab of slices. The pulse sequence further includes a series of fast spin echo readout excitation pulses applicable to the slab of slices such that MR data is acquired of the first set of slices during a first R-R interval and of the second set of slices during the next R-R interval.

In accordance with another aspect of the invention, an MR apparatus is disclosed. The apparatus includes an MRI system having a number of gradient coils positioned about a bore of a magnet to impress a polarizing magnetic field and an RF transceiver system, and an RF modulator controlled by a pulse control module to transmit RF signals to an RF coil assembly to acquire MR images. The MRI apparatus also includes a computer programmed to apply a pulse sequence having a first and a second inversion pulse during each heartbeat of a train of heartbeats and a series of readout excitation pulses during each heartbeat of the train of heartbeats. The computer is programmed to apply the pulse sequence such that at least one slice of data is acquired during each heartbeat of the train.

In accordance with yet another aspect of the invention, a computer readable storage medium having a computer program stored thereon is disclosed. The computer program represents a set of instructions that when executed by a computer causes the computer to generate and cause application of a non-selective inversion RF pulse to a slab of slices during successive R-R intervals. The computer generates an application of a slice-selective re-inversion RF pulse to the slab of slices during the successive R-R intervals. The computer is also programmed to delay data acquisition in each R-R interval by an inversion time sufficient to allow magnetization of blood within the slab to substantially reach a null point and, thereafter, apply a series of RF excitations in each R-R interval to acquire MR data for at least one slice in the slab in each R-R interval.

As the present invention may be embodied in a computer program as set forth above, the present invention may also take the form of a computer data signal that is embodied in a carrier wave and downloadable/uploadable to an MR imaging system. The signal includes at least a pulse sequence to be carried out for data acquisition by the MR imaging system. The pulse sequence includes a non-selective inversion pulse to be carried out in each R-R interval of a train of R-R intervals as well as a slice-selective re-inversion pulse to be carried out after the non-selective inversion pulse in each R-R interval. The pulse sequence further includes a set of excitation pulses to be applied in each R-R interval such that MR data may be acquired for at least one slice in a slab during each R-R interval.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
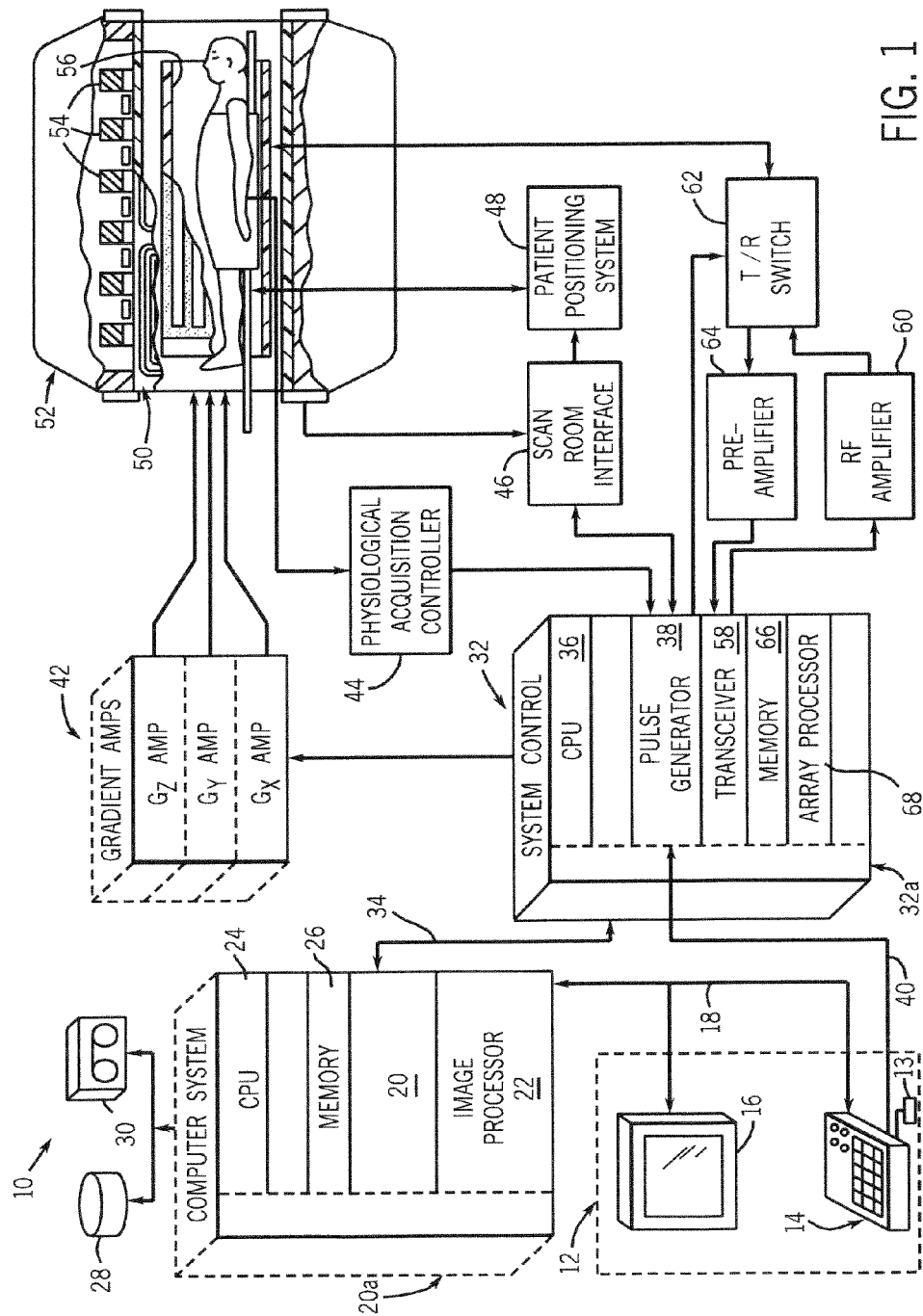
FIG. 1 is a schematic block diagram of an MR imaging system for use with the present invention.

Referring to FIG. 1, the major components of a preferred magnetic resonance (MR) imaging system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention includes a method and system suitable for use with the above reference MR system, and a pulse sequence applicable by the above referenced MR system, or any similar or equivalent system for obtaining MR images. The present invention includes a technique for efficient multi-slice acquisition with black blood contrast during successive R-R intervals.

Figure 2:
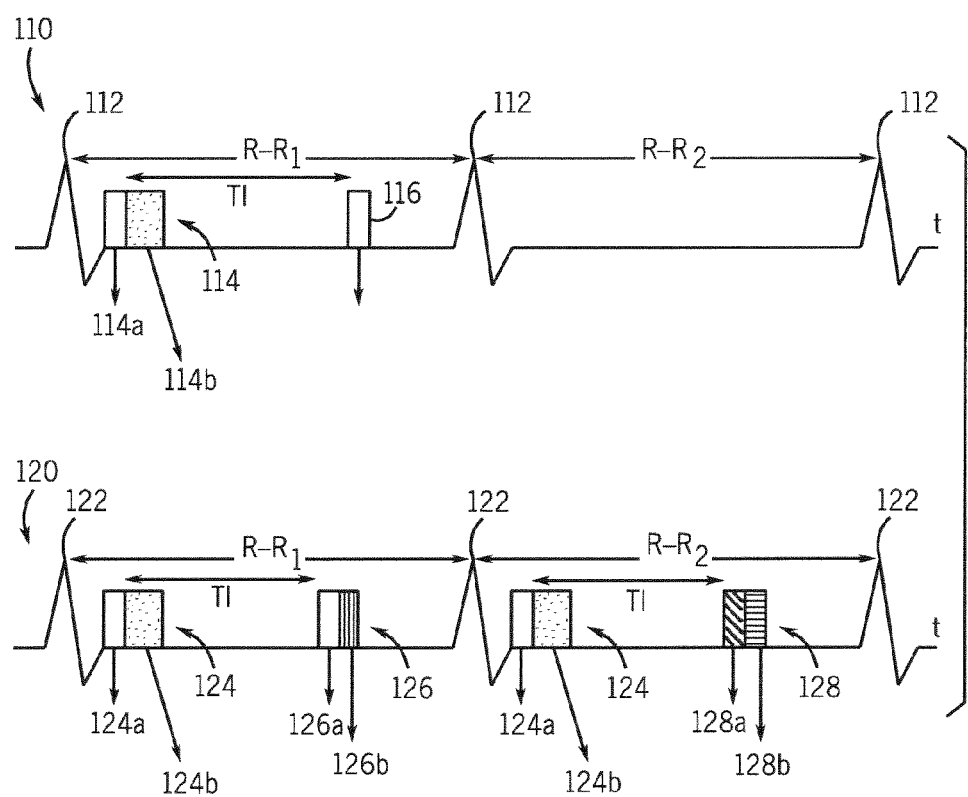
FIG. 2 is a is a graphical representation of a pulse sequence diagram comparing a conventional FSE sequence with black blood contrast with a multi-slice gated FSE sequence with black blood contrast in successive R-R intervals in accordance with the present invention.

Referring to FIG. 2, a pair of ECG gated pulse sequences 110, 120 are shown on a common time axis t. Referring first to pulse sequence 110, which schematically shows a conventional ECG-gated black blood sequence, after an ECG trigger 112 of an R-R interval or heartbeat, a preparation sequence 114 is applied. Preparation sequence 114 includes a non-selective inversion pulse 114a followed by a slice-selective re-inversion pulse 114b that is slice-selective only for the imaged slice. After an inversion time TI, RF excitation pulses 116 are applied to acquire data for a single spatial location. Inversion time TI is selected to be of sufficient length to allow the magnetization of blood within the to-be-acquired slice reaches a null before data acquisition.

In the conventional ECG-gated black blood sequence 110 using double inversion pulses 114a, 114b schematically shown in FIG. 2, it should be noted that data is acquired from a single slice in the first R-R interval, and equilibrium magnetization is allowed to recover in the next heartbeat or R-R interval. As such, during this relaxation heartbeat, MR data is not acquired. Accordingly, with the conventional black blood sequence, data can only be acquired in every other heartbeat until all k-space data is acquired. As is customary, in order to minimize respiratory artifacts, images are typically acquired during an end-expiratory breath-hold. Further, in order to achieve sufficient coverage, typically eight to twelve contiguous slices are acquired in successive breath-holds. In this regard, with the conventional ECG-gated black blood sequence 110 illustrated, repeated breath-holds are required to acquire a set of slices, one slice being acquired per breath-hold.

The pulse sequence 120 of the present invention is similarly triggered by the start of an R-R interval 122 that defines the beginning of each data acquisition window and includes a preparation sequence 124 that includes a non-selective inversion pulse 124a applicable across a slab of slices to invert spins in a longitudinal direction across the entire imaging volume. The non-selective inversion pulse 124a is immediately followed by a slice-selective re-inversion pulse 124b applicable to the slab of slices excited by the non-selective inversion pulse 124a so that the slab of slices is "re inverted". In a preferred embodiment, the slice-selective inversion pulse 124b has a spatial coverage greater than a slab encompassing all the slices to account for mis-registration between excitation and acquisition. An inversion time TI is selected such that data acquisition does not commence until the magnetization of the blood in the slab reaches the null point. After inversion time TI has passed, a series of excitation pulses 126 is applied to acquire data for one or more spatial locations. When data for multiple slices is to be acquired in the R-R interval, a first set of excitation pulses 126a is used to acquire data for a first slice and a second set of excitation pulses 126b is used to acquire data for a second slice. As such, more than one spatial location may be imaged in each heartbeat. This pulse sequence is substantially repeated during each R-R interval such that data is acquired during each R-R interval. Accordingly, data acquisition efficiency improves with reduced patient fatigue when acquiring the MR data.

As noted above, pulse sequence 120 is substantially repeated during each R-R interval. That is, a pulse sequence is applied during each heartbeat or R-R interval of a train of heartbeats or R-R intervals such that data is acquired during each heartbeat. However, in one preferred embodiment, one set of slices in the slab is acquired during a first R-R interval whereas another set of slices in the slab is acquired in the next R-R interval. For instance, in the example illustrated in FIG. 2, excitation pulses 126a and 126b are applied in interval R-R$_1$ to acquire data for two slices in the slab. In the next heartbeat defined by interval R-R$_2$, a series of excitation pulses 128 is applied. In this regard, excitation pulses 128a and 128b are used to acquire data for two other slices in the slab. As such, if the slab is defined as having four slices, then two slices of data will be acquired during interval R-R$_1$ whereas the remaining two slices of data will be acquired during interval R-R$_2$.

At the expiration of interval R-R$_2$, as defined by another ECG trigger 122, interval R-R$_3$ (not shown) begins, whereupon the excitation pulses applied during interval R-R$_1$ are repeated after the inversion pulses 124 and TI. It therefore follows that during interval R-R$_4$ (not shown), the excitation pulses 128 that were applied during interval R-R$_2$ are applied to acquire MR data after inversion pulses 124 and TI. As such, the tissue in each slice is excited only during every other R-R interval and hence there is little, if any, T$_1$ relaxation-based SNR loss. However, as noted above, data is acquired during each R-R interval thereby reducing scan time which advantageously may reduce patient fatigue since multiple slices of MR data may be acquired in a single breath-hold and increases patient throughput.

One skilled in the art will appreciate that the illustration of two separate slices of data being acquired in each R-R interval illustrates one embodiment of the invention. As such, it is contemplated that one or more than two slices of data may be acquired during each heartbeat or R-R interval.

It should be noted that the inversion time TI for pulse sequence 120 is shorter than the inversion time TI of pulse sequence 110. In this regard, the acquisition of data for the first slice 126a occurs during late-systole/early diastole. In a further embodiment, the start of the sequence, i.e. application of the non-selective inversion pulse 124a, is staggered by approximately 100 to 150 msec. so as to reduce slice mis-registration and a resulting loss of tissue signal as the re-inversion pulse 124b is played out during late diastole. Moreover, one skilled in the art will appreciate that if peripheral pulse gating is utilized, the need for the aforementioned shift in application of the non-selective inversion pulse may be obviated because of the inherent delay between a peripheral pulse and the R-wave of the order of 100 msec.

The present invention provides a method for improving the efficiency of double inversion recovery black blood imaging. In this regard, data acquisition occurs in every heartbeat to improve data acquisition efficiency. Further, inversion pulses are played out every heartbeat or R-R interval but imaging of a given slice occurs in every other heartbeat so as to maintain SNR. Additionally, the invention provides for single slab re-inversion to reduce the effects associated with motion related mis-registration. The present invention also allows for the acquisition of multiple slices of MR data in a single R-R interval so as to further reduce total scan time.

Accordingly, the present invention includes a method of multi-slice image acquisition with black blood contrast that includes a non-selective inversion pulse and a re-inversion pulse that is slice-selective over a region encompassing a plurality of slice selections. The method includes timing execution of a series of RF excitation pulses such that signal from black blood is near a null point to acquire data for each spatial slice. Moreover, the method supports single or multi-slice data acquisition in successive R-R intervals.

The re-inversion pulse is applied over the entire slab having all slice selections and data is acquired for a first set of slice selections in a first R-R interval and a second set of slice selections in the next R-R interval.

The present invention also includes a computer program for multi-slice coverage in a single acquisition with black blood T$_2$ weighted image contrast. The computer program has a set of instructions that when executed by a computer, cause the computer to generate and cause application of a non-selective inversion RF pulse to a slab of slices. The computer program also causes the computer to generate and cause application of a slice-selective re-inversion RF pulse and apply an inversion time so that a null point of blood within the slab occurs prior to data acquisition. A series of RF excitation pulses is applied and MR data is acquired for a first set of slices in the slab in a first R-R interval and a second set of slices in the slab in the next R-R interval. Preferably, data for each set of slice selections is reacquired every other R-R interval; however, data is acquired during each R-R interval.

The present invention also includes an MR apparatus to produce consistent contrast in FSE image acquisition. The apparatus includes an MRI system having a number of gradient coils positioned about a bore of a magnet to impress a polarizing magnetic field and an RF transceiver system, and an RF modulator controlled by a pulse control module to transmit RF signals to an RF coil assembly to acquire MR images. The apparatus also includes a computer programmed to apply a pulse sequence having a non-selective inversion pulse to invert spins in a longitudinal direction across an entire slab of slices and a slab selective re-inversion pulse. The inversion and re-inversion pulses are played out during each R-R interval during data acquisition. The pulse sequence applied by the computer also has a series of excitation pulses having fast spin echo readout spaced apart from the slice-selective re-inversion pulse by an inversion time to acquire data for at least one slice in the slab in each R-R interval.

The present invention also includes a pulse sequence for use in multi-slice MR data acquisition. The pulse sequence includes a non-selective inversion pulse applicable to a slab of slices, and a slab selective re-inversion pulse applicable to those slices. The pulse sequence also includes a series of fast spin echo readout excitation pulses applicable to a first number of slices in the slab after an inversion time during a first R-R interval. Additional or, preferably, remaining slices in the slab are acquired in the next R-R interval. Preferably, the aforementioned inversion time is selected so that blood in the slab is at or near the null point.

As noted above, the present invention may take the form of a computer program that when executed by a computer causes the computer to initiate a pulse sequence as heretofore described. However, the present invention may equivalently take the form of a computer data signal may be downloaded or uploaded to an MR imaging system. In this regard, the data signal, which may be embodied in a carrier wave, represents at least a pulse sequence to be carried out for data acquisition by the MR imaging system. The pulse sequence may include or be defined by a non-selective inversion pulse to be carried out in each R-R interval of a train of R-R intervals. The pulse sequence may further be defined by or include a slice-selective re-inversion pulse to be carried out after the non-selective inversion pulse in each R-R interval. A set of excitation pulses is to be applied in each R-R interval such that MR data may be acquired for at least one slice in a slab during each R-R interval of the train of R-R intervals.

The present invention has been described in terms of the preferred embodiment, and it is recognized that equivalents, alternatives, and modifications, aside from those expressly stated, are possible and within the scope of the appending claims.

What is claimed is:

1. A method of multi-slice image acquisition with black blood contrast, the method comprising the steps of:
    applying a non-selective inversion pulse in successive R-R intervals;
    applying a re-inversion pulse in the successive R-R intervals that is slice-selective over a region encompassing a plurality of slice selections;
    timing execution of a series of RF excitation pulses such that signal from blood is near a null point in each R-R interval; and
    acquiring data of at least two slices for each application of the re-inversion pulse in the successive R-R intervals.

2. The method of claim 1 wherein the plurality of slice selections includes two sets of slice selections and further comprising the step of acquiring data for a first set of slice selections in a first R-R interval and acquiring data for a second set of slice selections in a next R-R interval.

3. The method of claim 2 wherein each set includes two slice selections using a fast spin echo readout.

4. The method of claim 2 further comprising the step of alternating data acquisition of the two sets of slice selections until k-space is filled.

5. The method of claim 1 further comprising the step of acquiring more than one slice of MR data per patient breath-hold.

6. The method of claim 5 further comprising the step of acquiring four slices of MR data per patient breath-hold.

7. A computer readable storage medium having a computer program stored thereon, the computer program representing a set of instructions that when executed by a computer causes the computer to:
    generate and cause application of a non-selective inversion pulse applicable to a slab of slices, the non-selective inversion pulse to be applied in each R-R interval;
    generate and cause application of a slice-selective re-inversion pulse applicable to the slab of slices applied after each non-selective inversion pulse; and
    generate and cause application of a series of spin echo readout excitation pulses applicable to the slab of slices such that MR data with black blood contrast is acquired of a first set of at least two slices of the slab during a first R-R interval after application of a respective single slice-selective re-inversion pulse and of a second set of at least two slices of the slab during a next R-R interval after application of a respective single slice-selective re-inversion pulse.

8. The computer readable storage medium of claim 7 wherein the set of instructions further cause the computer to delay for a TI period between generation and application of the re-inversion pulse and the series of excitation pulses in each R-R interval sufficient in length to allow magnetization of blood in the slab to substantially reach a null point before data acquisition.

9. The computer readable storage medium of claim 7 wherein the at least two slices of the first set are different from the at least two slices of the second set.

10. The computer readable storage medium of claim 7 wherein the set of instructions further cause the computer to acquire data for more than one slice during a single patient breath-hold.

11. An MRI apparatus comprising:
    a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and
    a computer programmed to apply a pulse sequence having a first and a second inversion pulse during each heartbeat of a successive train of heartbeats and a series of readout excitation pulses during each heartbeat of the successive train of heartbeats such that at least two slices of data with black blood contrast are acquired for each application of one of the first and the second inversion pulses during each heartbeat of the successive train of heartbeats.

12. The MR apparatus of claim 11 wherein the first inversion pulse is a non-selective 180 degree pulse and the second inversion pulse is a selective 180 degree pulse designed to re-invert magnetization in a slab containing a plurality of slices.

13. The MR apparatus of claim 12 wherein the pulse sequence is further configured to acquire MR data for multiple slices in each heartbeat of the train of heartbeats.

14. The MR apparatus of claim 13 wherein the slices in a first heartbeat are different from that of a next heartbeat.

15. The MR apparatus of claim 11 wherein the computer is further programmed to apply the pulse sequence such that a plurality of slices of MR data is acquired in a single patient breath-hold.

16. The MR apparatus of claim 11 wherein the pulse sequence further includes a TI period between the re-inversion pulse and the series of excitation pulses in each R-R interval sufficient in length to allow magnetization of blood in the slab to substantially reach a null point before data acquisition.

17. A computer readable storage medium having a computer program stored thereon, the computer program representing a set of instructions that when executed by a computer causes the computer to:
generate and cause application of a non-selective inversion RF pulse to a slab of slices during successive R-R intervals;
generate and cause application of a slice-selective re-inversion RF pulse to the slab of slices during successive R-R intervals;
delay data acquisition in each R-R interval by an inversion time sufficient to allow magnetization of blood within the slab to substantially reach a null point;
apply a series of RF excitation pulses in each R-R interval; and
acquire MR data for at least two slices in the slab for each slice-selective re-inversion RF pulse in each R-R interval.

18. The computer readable storage medium of claim 17 wherein the set of instructions further causes the computer to acquire data for two slices in the slab in each R-R interval.

19. The computer readable storage medium of claim 18 wherein the two slices of a first R-R interval is different from the two slices of a next R-R interval.

20. The computer readable storage medium of claim 19 wherein tissue for each slice in the slab is excited during every other R-R interval.

21. The computer readable storage medium of claim 17 wherein the set of instructions further causes the computer to acquire more than one slice of MR data in a single patient breath-hold.

22. The computer readable storage medium of claim 21 wherein the more than one includes four slices of data in a single patient breath-hold.

23. A computer readable storage medium having a computer program stored thereon, the computer program representing a set of instructions that when executed by a computer causes the computer to:
generate and cause application of a non-selective inversion pulse to be carried out in each R-R interval of a train of R-R intervals;
generate and cause application of a slice-selective re-inversion pulse to be carried out after the non-selective inversion pulse in each R-R interval; and
generate and cause application of a set of excitation pulses to be applied in each R-R interval such that MR data may be acquired for at least two slices in a slab during each R-R interval and for each slice-selective re-inversion pulse.

24. The computer readable storage medium of claim 23 wherein the wherein the set of instructions further cause the computer to incorporate an inversion recovery time in each R-R interval sufficient to allow magnetization of blood within the slab to substantially reach a null point.

* * * * *

UNITED STATES PATENT AND TRADEMARK OFFICE
CERTIFICATE OF CORRECTION

PATENT NO. : 7,412,277 B1
APPLICATION NO. : 10/604829
DATED : August 12, 2008
INVENTOR(S) : Saranathan et al.

Page 1 of 1

It is certified that error appears in the above-identified patent and that said Letters Patent is hereby corrected as shown below:

On the Title page at (75), delete "Savin" and substitute therefore -- Slavin --.

Signed and Sealed this

Twenty-eighth Day of October, 2008

JON W. DUDAS
*Director of the United States Patent and Trademark Office*